(12) United States Patent
Zahradnik et al.

(10) Patent No.: US 6,838,264 B2
(45) Date of Patent: Jan. 4, 2005

(54) ANTIBODIES AND PEPTIDE ANTIGENS FOR PRODUCING ANTIBODIES HAVING A SELECTIVE BINDING SPECIFICITY TO BIOACTIVE INTACT PARATHYROID HORMONE (PTH) 1-84

(75) Inventors: Richard J. Zahradnik, Dana Point, CA (US); Jeffrey R. Lavigne, San Juan Capistrano, CA (US)

(73) Assignee: Immutopics, Inc., San Clemente, CA (US)

( * ) Notice: Subject to any disclaimer, the term of this patent is extended or adjusted under 35 U.S.C. 154(b) by 254 days.

(21) Appl. No.: 09/730,174

(22) Filed: Dec. 5, 2000

(65) Prior Publication Data

US 2002/0110871 A1 Aug. 15, 2002

(51) Int. Cl.[7] ............................ C12P 21/08; A61K 38/04; C07K 17/02
(52) U.S. Cl. .................... 435/70.21; 435/7.1; 435/331; 530/388.1; 530/388.15; 530/388.24; 530/389.2; 530/327; 530/412; 530/413
(58) Field of Search ..................... 530/388.1, 388.24, 530/389.2, 391.1, 391.5, 388.15, 412, 413, 327; 435/70.21, 810, 7.1, 331

(56) References Cited

U.S. PATENT DOCUMENTS

| 4,341,755 | A | * | 7/1982 | Lindall et al. | |
| 6,107,049 | A | * | 8/2000 | Allard et al. | |
| 6,689,566 | B1 | * | 2/2004 | Cantor et al. | 435/7.1 |

FOREIGN PATENT DOCUMENTS

| WO | 0042437 | 7/2000 |

OTHER PUBLICATIONS

Kuby et al. Immunology, Second edition, pp. 86–96, 1994.*
Colman et al. A structural view of immune recognition by antibodies, pp. 33–36, 1994.*
Abaza et al. J of Protein Chemistry 11(5) 433–444, 1992.*
Harlow et al in Antibodies a Laboratory Manual, 1988, Cold Spring harbor laboratory publication, Cold Spring Harobr, NY, pp. 92–94, and pp. 323–358.*
Ratcliffe et al, J Immunol Methods 127(1): 109–16, Feb. 1990.*
Ikeda et al, J Clin Endo & Metabolism 79(6): 1322–27, 1994.*
Heinrich et al. J Biol Chem 259(5): 3320–3329, Mar. 1984.*
Scantibodies Laboratory, Inc., *New PTH Analytes CAP and CAP/CIP Ratio and Their Clinical Benefits*, no date, advertising brochure, 4 pages.
Markus R. John, et al., *A Novel Immunoradiometric assay Detects Full–Length Human PTH but not Amino–Terminally Truncated Fragments: Implications for PTH Measurements in Renal Failure*, copyright 1999, The Journal of Clinical Endocrinology and Metabolism, vol. 84, No. 11, pp. 4287–4290.
Samuel R. Nussbaum, et al., *Highly Sensitive Two–Site Immunoradiometric Assay of Parathyrin and Its Clinical Utility in Evaluating Patients with Hypercalcemia*, Aug., 1987, Clinical Chemistry, vol. 33, No. 8, pp. 1364–1367.
Gino V. Segre, MD. et al., *Intact PTH (IRMA) II. New applications to Issues in Parathyroid Hormone and Mineral Metabolism*, no date, Nichols Institute, 8 pages.

* cited by examiner

*Primary Examiner*—Christina Chan
*Assistant Examiner*—Phuong Huynh
(74) *Attorney, Agent, or Firm*—Stetina Brunda Garred & Brucker (57) ABSTRACT

Peptide antigens corresponding to amino acid residues 2–12, 1–12, 2–15 and 1–15 of parathyroid hormone (PTH), antibodies having an affinity to such peptide antigens and methods of producing the same. Such antigens, antibodies and methods producing the same according to the present invention are useful in determining bioactive intact PTH levels in serum, plasma, and/or cell culture media. Such antibodies further possess a high degree of species cross-reactivity, but substantially mitigated cross-reactivity to non-whole PTH peptide fragments and little to no recognition of the first amino acid residue of PTH.

5 Claims, 4 Drawing Sheets

ANTIBODIES AND PEPTIDE ANTIGENS FOR PRODUCING ANTIBODIES HAVING A SELECTIVE BINDING SPECIFICITY TO BIOACTIVE INTACT PARATHYROID HORMONE (PTH) 1-84

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

Parathyroid hormone (PTH) and its importance in regulating the concentration of calcium ions in the blood is well-known. In this regard, such hormone is created by the parathyroid glands and, in combination with other factors, functions to regulate the blood calcium ion levels such that the same is maintained in a steady concentration in both cells and surrounding fluids. Essentially, PTH functions to release stored calcium in the body when serum calcium levels decrease. On the other hand, such secretion is suppressed to the extent the serum calcium concentration increases.

In its complete form PTH comprises a unique peptide comprised of 84 amino acids. The specific sequence of PTH, as provided for a plurality of species, namely, humans, rats, mice, bovids, dogs and pigs, are depicted in FIG. 1, and a variation thereof in FIG. 2, which illustrates the relatively consistent structure such hormone maintains between such identified species.

Given its significance in calcium metabolism for not only humans, but a variety of species, accurately measuring PTH has and continues to be of substantial clinical significance. As is well-documented, serum PTH levels serve as an important parameter for patients having diseases such as hypercalcemia, primary hyperparathyroidism and osteoporosis, among many others. PTH likewise becomes of substantial clinical importance in patients afflicted with chronic renal failure who, because of an excess in PTH production, can develop renal osteodystrophy.

Notwithstanding its important role in metabolism and clinical significance, substantial difficulties have and continue to exist with regard to determinating circulating biologically active PTH levels. First of all, it is well-known that PTH is normally present at extremely low levels, which are normally between 10 pg/ml to 65 pg/ml. Furthermore, it is known that the PTH peptide can be present in a variety of circulating PTH fragments, and in particular large non-(1–84) circulating PTH fragments which appear to co-migrate chromatographically with the (7–84) PTH molecule and are known to significantly interfere with conventional PTH assay measurements. Indeed, the large non-(1–84) PTH fragments may represent about one-half (½) of the PTH measured by a majority of current assays. Exemplary of the current shortcomings of the accurate measurement of PTH are set forth in published Patent Cooperation Treaty International Application No. PCT/US00/00855, International Publication No. W0/00/42437, entitled *Methods for Differentiating and Monitoring Parathyroid and Bone Status Related Diseases*, and Lepage, Raymond et al., *A Non-(1–84) Circulating Parathyroid Hormone (PTH) Fragment Interferes With Intact PTH Commercial Assay Measurement In Uremic Samples*, Clinical Chemistry 44:4, 1998 pages 805–809, the teachings of which are expressly incorporated herein by reference.

In an attempt to address such shortcomings, a new assay for detecting PTH levels was introduced by Scantibodies Laboratory, of Santee, Calif., which incorporates a tracer antibody having a binding specificity for the very end N-terminal fraction of human PTH, and more specifically, the first six amino acid residues thereof. As presently understood, such assay appears to minimize cross-reactivity with large non-(1–84) PTH fragments. However, to derive such antibodies requires substantial effort and expense in purifying the same. Moreover, such tracer antibodies have maximum recognition for only the first amino acid residue of PTH, and substantially reduced specificity for any subsequent residues thus obviating its use for some other species where the first amino acid is different. Such drawbacks are discussed in the article by John, M. R. et al., entitled *A Novel Immunoradiometric Assay Detects Full-Length Human PTH but not Amino-Terminally Truncated Fragments: Implications for PTH Measurements in Renal Failure*, The Journal of Clinical Endocrinology & Metabolism, Vol. 84, No. 11, 1999, p. 4287–4290, the teachings of which are expressly incorporated herein by reference.

Thus, there has been and continues to be a long felt need in the art for an assay binding partner and method of generating the same that is specific for bioactive intact PTH that can determine PTH levels with mitigated cross-reactivity to PTH peptide fragments. There is likewise a need in the art for improved PTH binding partners that can measure PTH levels in a more cost-effective manner and have a greater affinity for PTH that can be readily incorporated into immunoassay kits and the like. Still further there is a need for binding partners, namely, antibodies having a binding recognition that is specific to PTH and can be utilized to detect PTH levels over a wide-variety of species. Finally, there is a need in the art for an improved binding partner having a high binding affinity for PTH that may be readily derived using conventional mechanisms that requires minimal purification, results in greater binding recognition for intact PTH, possesses minimal cross reactivity to large non-(1–84) PTH fragments, and can be derived utilizing methods that generate higher antibody yields than prior art binding partners.

BRIEF SUMMARY OF THE INVENTION

The present invention specifically addresses and alleviates the above-identified deficiencies in art. In this regard, the present invention is directed to certain novel antigens, antibodies, and methods for producing antibodies that are useful in determining bioactive intact PTH levels in a sample fluid, such as serum, plasma or cell culture media. The antigens, antibodies and methods of the present invention have the particular advantages of possessing greater affinity for PTH, and in particular, are designed to have a novel recognition for amino acid residues extending beyond the first N-terminal PTH residue than prior art antibodies specific to bioactive intact PTH, and further have negligible cross-reactivity with the large non-(1–84) molecular forms of PTH. Moreover, the antigens, antibodies and methods of producing the same according to the present invention have substantial cross-reactivity with a wide variety of species, and may be utilized to detect PTH levels in not only humans, but also in rats, mice, bovids, dogs, and pigs.

According to a preferred embodiment, the antigen comprises the formula VAL-SER-GLU-ILE-GLN-X-MET-HIS- ASN-LEU-GLY wherein X is selected from the group consisting of LEU and PHE. With respect to such embodiment, such antigenic peptide represents amino acid residues 2–12 of PTH, with the sixth amino acid residue thereof being selective between 1 FU and PHE, the former occurring in the PTH of humans, rats, mice and pigs, on one hand, and the latter, being inherent in the PTH of bovines and dogs, on the other hand. In a more highly preferred embodiment, the antigen comprises a peptide having the formula Y-VAL-SER-GLU-ILE-GLN-X-MET-HIS-ASN-LEU-GLY wherein X is an amino acid residue selected between LEU and PHE, as discussed above, and Y is an amino acid residue consisting of either SER or ALA the former reflecting the amino acid present in humans, dogs, and pigs, and the latter being inherent in the PTH of rats, mice and bovines.

In further preferred embodiments, the antigen comprises the formula VAL-SER-GLU-ILE-GLN-X-MET-HIS-ASN-LEU-GLY-LYS-HIS-LEU wherein X is selected from the group consisting of LEU or PHE. Such antigenic peptide represents amino acid residues 2–15 of PTH, with the sixth amino acid residue comprising either LEU or PHE, to thus reflect the corresponding amino acid residue occurring in the appropriate species specified above. In a most highly preferred embodiment, the antigenic peptide represents amino acid residues 1–15 of PTH and comprises the formula Y-VAL-SER-GLU-ILE-GLN-X-MET-HIS-ASN-LEU-GLY-LYS-HIS-LEU, wherein X comprises amino acid residue LEU or PHE and Y is an amino acid residue consisting of either SER or ALA the latter being selective to correspond to a particular species identified above.

With respect to the antibodies and methods of producing the same according to the present invention, such are directed to antibodies having an affinity and specificity for the aforementioned antigens. Preferably, the antibodies are specific to amino acid residues 2–12, 1–12, 2–15 and 1–15, respectively, of PTH and are preferably produced via the steps of administering a peptide antigen of the aforementioned variety to a host animal, which preferably comprises a goat, to produce antibody production against the peptide antigen. In an alternative, preferred embodiment, antibody production is induced via the administration of larger peptide fragments of PTH. Preferably, such PTH fragment may comprise (1–34) PTH, which may further optionally include a carrier protein covalently linked or fused thereto to increase antigenicity or intact (1–84) PTH. To the extent antibodies are sought to be derived to detect PTH in humans, the intact (1–84) PTH molecule preferably comprises intact rat PTH or, to a lesser extent, human PTH. The antibody titer produced by the administration of the antigen to the host animal is then monitored. Thereafter, antisera produced in the host animal is then isolated and selected such that the antibodies thereof having specificity for the desired antigenic region of PTH (i.e., amino acid residues 2–12, 1–12, 2–15 and 1–15 of PTH, respectively) are isolated and thereafter purified. The antibodies may then be labeled or otherwise incorporated into any of a variety of conventional assays for use in the detection of PTH, whether it would be for humans or any of a variety of species.

As will be recognized by those skilled in the art, the antigens, antibodies and methods of the present invention, by focusing on amino acid residues 2–12, 1–12, 2–15 and 1–15 of PTH, respectively, focus on that portion of the PTH molecule possessing the highest degree of N-terminal biological activity, and thus maximize detection of the same. Moreover, with respect to the more highly preferred embodiments, by providing antigens, antibodies and methods of producing the same that are inclusive of other amino acid residues extending beyond the N-terminal biologically active site (i.e., up to and including the twelfth (12th) and fifteenth (15th) amino acid residues of PTH), the specificity and affinity of such antibodies are thus more highly refined and enable the same to detect PTH levels with greater specificity than prior art receptors, as incorporated into assays and the like. Perhaps most importantly, however, the antibodies produced according to the present invention (as well as the methods and peptide antigens disclosed herein for achieving that end) have substantially minimized cross-reactivity to large non (1–84) PTH peptide fragments, do not possess maximum recognition for only the first amino acid residue of PTH, and further, may be readily derived in a cost-effective manner insofar as the antibody yields generated from methods of the present invention should be greater than prior art methods.

It is therefore an object of the present invention to provide novel antigens for the production and isolation of antibodies, antibodies and methods of producing antibodies that have a binding affinity and specificity for PTH that possess mitigated cross-reactivity to large non (1–84) PTH peptide fragments.

Another object of the present invention is to provide novel antigens for the production of antibodies, antibodies and methods of producing antibodies that have a greater affinity and specificity for PTH than prior art binding partners and further, possess a higher degree of cross reactivity between inter-species PTH such that the antigens, antibodies and methods producing the same according the present invention can be readily utilized for the detection of PTH in a variety of species.

Another object of the present invention is to provide novel antigens for the production and isolation of antibodies, antibodies and methods of producing antibodies which have a binding affinity and specificity for more of the biologically active N-terminal portion of PTH and, hence, are more effective and accurate in determining bioactive intact PTH levels than prior art binding partners directed thereto.

Another object of the present invention is to provide novel antigens for the production and isolation of antibodies, antibodies and methods of producing antibodies which do not possess a maximum binding affinity for only the first N-terminal amino acid residue of PTH.

Another object of the present invention is to provide novel antigens for the production and isolation of antibodies, antibodies and methods of producing antibodies that are less expensive to produce and generate higher antibody yields than prior art methods for producing antibodies having a binding affinity and specificity for PTH.

Still further objects of the present invention are to provide novel antigens for the production of antibodies, antibodies and methods of producing antibodies which readily derive antibodies which may be readily incorporated into any of a variety of commercially-available assays and further, can be modified (e.g., to include a label, and the like) as may be desired for any of a variety of immunoassay applications.

BRIEF DESCRIPTION OF THE DRAWINGS

These, as well as other features of the present invention, will become more apparent upon reference to the drawings wherein:

FIG. 1 depicts the amino acid sequence of PTH for a variety of species, namely humans, rats, mice, bovines, dogs and pigs and further depicts amino acid sequences identified herein as SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, and SEQ ID NO. 12.

DETAILED DESCRIPTION OF THE INVENTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Figure 2:
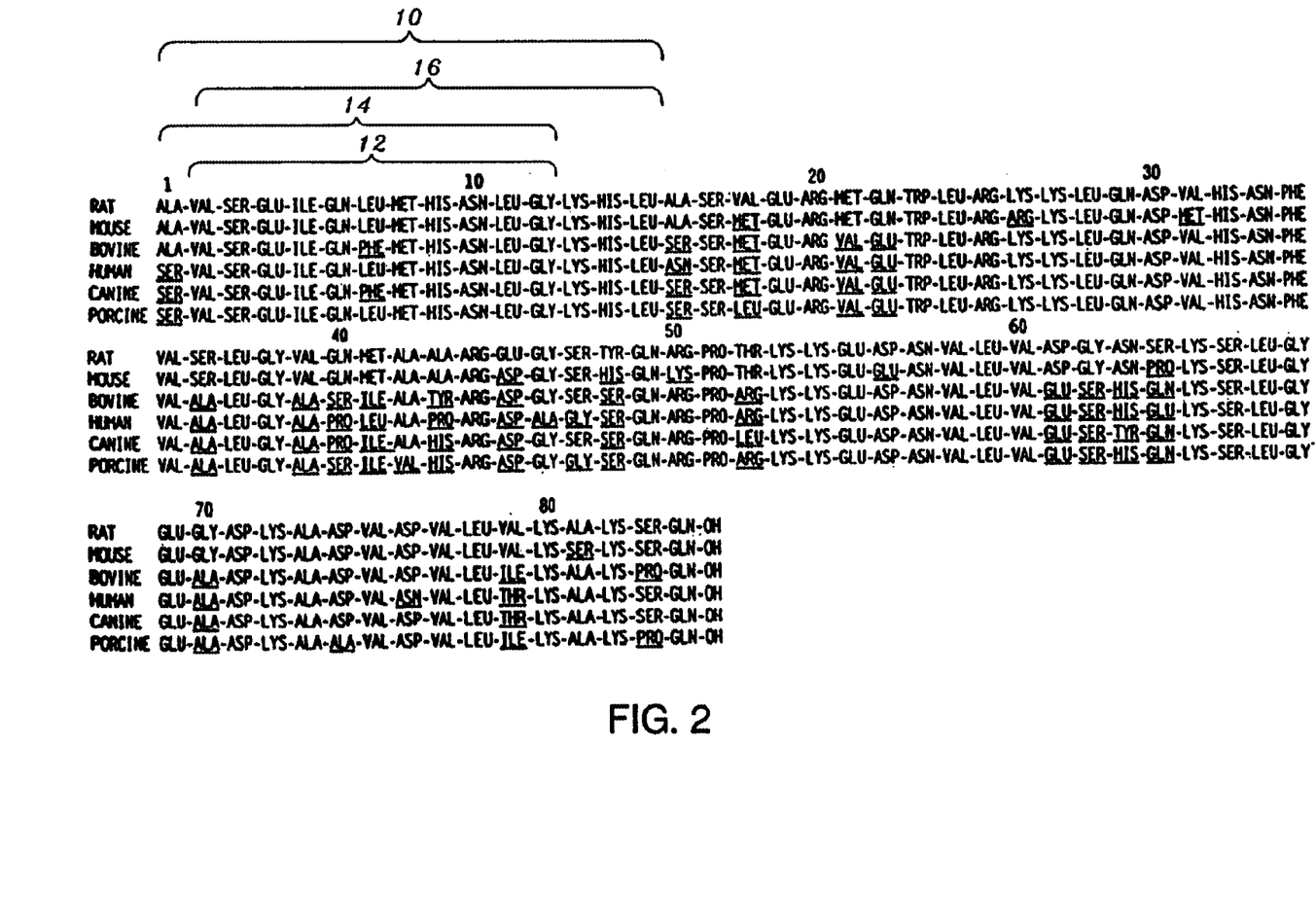
FIG. 2 is an alternate illustration of FIG. 1 depicting a variation of the 1–84 amino acid sequence of PTH of the aforementioned species, yet depicting the conserved N-terminus of PTH wherein the amino acid sequences of SEQ ID NOS. 1–12 remain constant.
Figure 3:
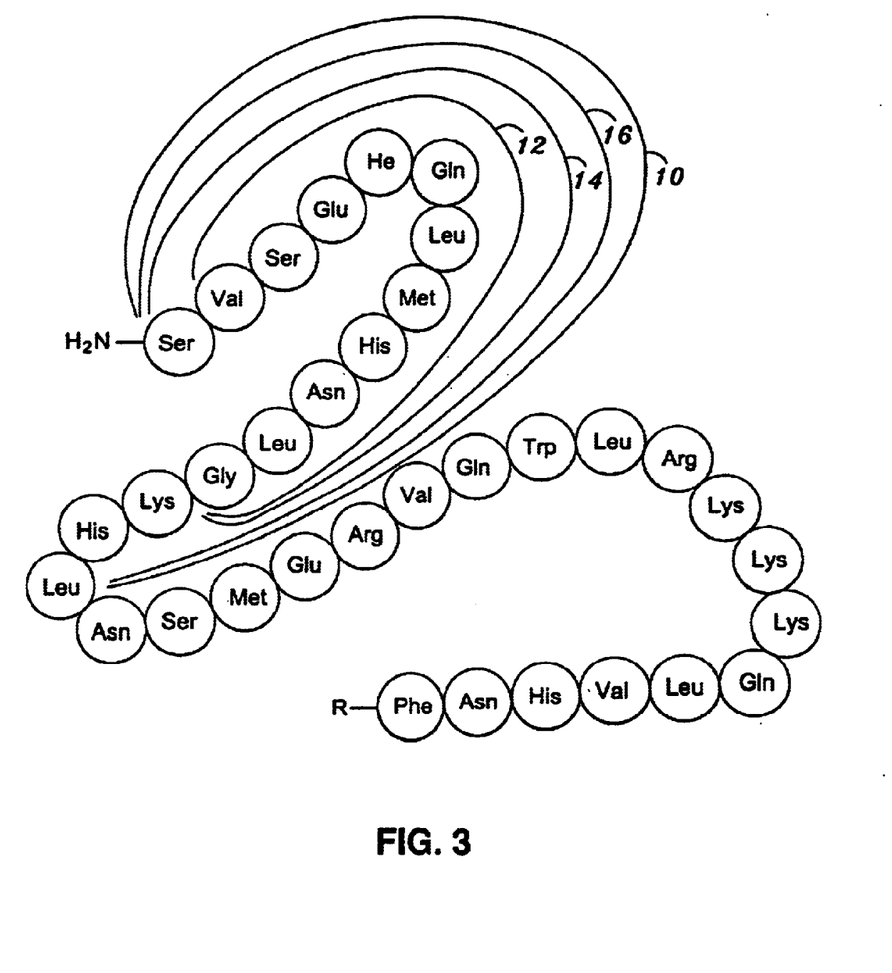
FIG. 3 is a diagrammatical view of the N-terminal portion of human PTH.

The present invention encompasses antigens, antibodies and methods of producing antibodies that are directed to an antigenic region of PTH positioned in the N-terminal region thereof, and more precisely, the first fifteen (15) amino acid residues extending from the N-terminal depicted as 10 in FIGS. 1–3. As is well-known, the N-terminal region of PTH is recognized as necessary for PTH/PTHrp receptor binding, and is further recognized as being most desireable epitope for measuring bioactive intact PTH levels, as may be found in a biological fluid sample, such as serum, plasma or cell culture media. Indicative of the current state of the art associated with PTH and the methods of detecting the same are discussed at length in published Patent Cooperation Treaty International Application No. PCT/US00/00855, International Publication No. WO/00/42437, entitled *Methods for Differentiating and Monitoring Parathyroid and Bone Status Related Diseases*, and Lepage, Raymond et al., *A Non-(1–84) Circulating Parathyroid Hormone (PTH) Fragment Interferes With Intact PTH Commercial Assay Measurement In Uremic Samples*, Clinical Chemistry 44:4, 1998 pages 805–809, the teachings of which are expressly incorporated herein by reference.

According to a preferred embodiment, the antigenic peptide of the present invention comprises those amino acid residues corresponding to amino acid residues 2–12 of PTH, collectively identified as 12 in FIGS. 1–3. Specifically, such antigenic peptide will have the formula:

VAL-SER-GLU-ILE-GLN-X-MET-HIS-ASN-LEU-GLY wherein X is an amino acid residue selected from either LEU or PHE. As will be recognized by those skilled in the art, the sixth (6th) amino acid residue of this PTH peptide fragment does differ between the cited species whereby such residue comprises LEU in humans, rats, mice and pigs, on one hand, but PHE for bovids and dogs on the other. As will be appreciated by those skilled in the art, notwithstanding the single amino acid residue difference, such antigenic peptide remains otherwise constant between the cited species which, as discussed more fully below, can enable antibodies to be prepared and ultimately utilized that are cross-reactive and, hence, effective in detecting PTH levels in a variety of such species.

In a more highly preferred embodiment, the peptide antigen reflects the first twelve (12) amino acid residues of PTH, identified as 14, and comprises the formula:

Y-VAL-SER-GLU-ILE-GLN-X-MET-HIS-ASN-LEU-GLY wherein X is an amino acid residue selected from either LEU or PHE and Y is an amino acid residue selected from either SER or AlA. With respect to the variation at the first amino acid residue, it will he readily appreciated that such antigenic peptide may be formed such that such amino acid comprises SER, as found in humans, dogs and pigs, or ALA, as found in rats, mice and bovids. In this respect, the variation provided for in the antigenic peptide in the present invention, and in particular the more highly preferred embodiments thereof, provide leeway such that the antibodies ultimately derived from such antigenic peptides may be formed to possess a higher binding affinity as may be desired to detect PTH in a given species.

In more highly refined embodiments of the present invention, the antigenic peptides comprise sequences that correspond to amino acid residue 2–15 and 1–15, respectively, of PTH. With regard to the former, identified in FIGS. 1–3 as 16, such antigenic peptide will have the formula: VAL-SER-GLU-ILE-GLN-X-MET-HIS-ASN-LEU-GLY-LYS-HIS-LEU wherein X is an amino acid residue selected from either LEU or PHE With respect to the latter embodiment corresponding to amino acid residues 1–15 of PTH, identified as 10, such antigenic peptide will have the formula: Y-VAL-SER-GLU-ILE-GLN-X-MET-HIS-ASN-LEU-GLY-LYS-HIS-LEU wherein X is an amino acid residue selected from either LEU or PHE and Y is an amino acid residue selected from either SER or ALA. Notwithstanding the foregoing formulas for the aforementioned antigenic peptides, it will he recognized that the same will extend to all functional derivatives thereof, which is meant to include functionally comparable peptides derived from the same region of PTH. as reflected in the sequences of FIGS. 1–3, and having a similar ability to induce specific anti-PTH antibodies, and more particularly antibodies specific to the N-terminal amino acid residues of PTH. In this regard, such functional derivative may be similarly positioned peptides or peptides derived from the sequences discussed above and reflected in FIGS. 1–3 having substitutions, additions or deletions of amino acids, provided the derivation does not alter the ability of the peptide antigen to induce antibody reactive to PTH.

It should further be recognized that the peptide antigens of the present invention include those peptides whose amino acid sequence may be shifted within a few amino acids upstream or downstream of the antigenic peptides discussed above in FIGS. 1–3, as well as those peptides having conservative amino acid changes such that substitutions, additions or deletion of amino acids or changes do not significantly effect the ability of the peptide antigen to induce antibodies with high affinity and specificity for the first twelve amino acid residues of PTH , or any subcomponents thereof.

Figure 4:
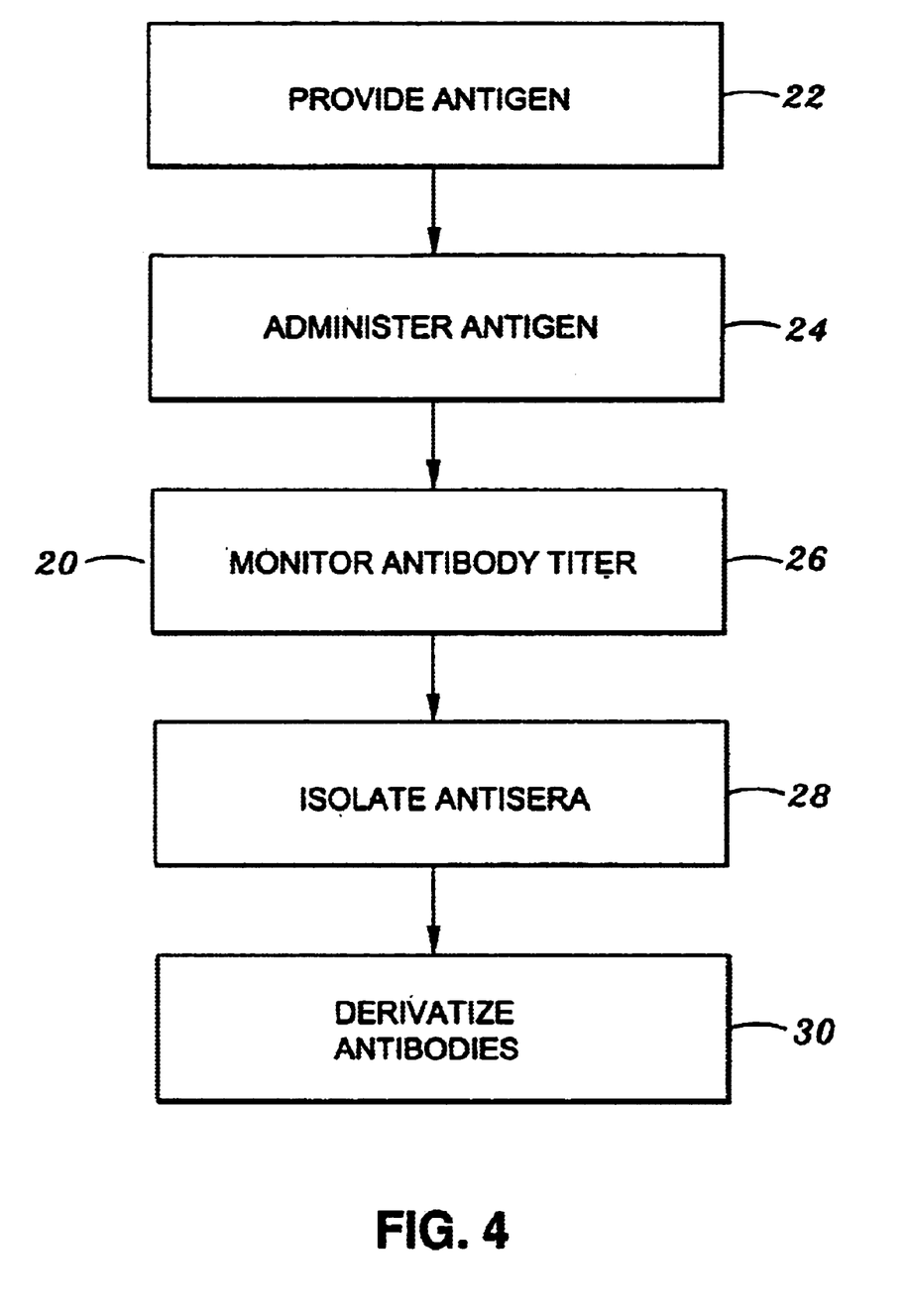
FIG. 4 is a flow chart depicting the steps for producing antibodies according to a preferred embodiment of the present invention.

With regard to antibody production, there is illustrated in FIG. 4 the method 20 of generating the same. Initially, there is provided a peptide 22 of the aforementioned variety which corresponds to all or a portion of the first twelve (12) to fifteen (15) amino acid residues of PTH of a given species. According to a more highly preferred embodiment, however, the antigenic peptide utilized to generate antibody production will include larger PTH fragments, including but not limited to the (1–34) PTH and the entire intact (1–84) PTH peptide. Along these lines, while the antibodies ultimately produced will have specificity to those amino acid residues corresponding to the aforementioned antigenic peptides (i.e., amino acid sequencing 2–12, 1–12, 2–15 and/or 1–15 of PTH) within the method of the present invention, at least with respect to the initial step of providing an antigen 22 and subsequently administering the same, via step 24 discussed below, it will be appreciated that the entire PTH peptide and any fragment thereof can preferably serve as a suitable antigenic peptide to induce the production of antibodies which will ultimately possess the ideal binding affinity and specificity for the biologically active portion of PTH at the N-terminal thereof. In a most highly preferred embodiment, the antigenic peptide provided and administered will comprise the PTH fragment corresponding to amino acid residues 1–34 of PTH, which may optionally be coupled to a carrier protein. Such peptide fragment may alternatively preferably be administered as whole length (1–84) PTH, which may take the form of any of the species identified in FIGS. 1 and 2. Preferably, in the context of developing antibodies specific for human PTH, the use of (1–34) rat PTH or whole length (1–84) rat PTH is preferred.

Such antigenic peptides may be produced by any of a variety of methods well-known in the art, including synthesis by conventional methods, such as solid-phase chemical synthesis or by recombinant technology. As will be further appreciated, the synthetic peptides may optionally be chemically coupled to a carrier protein or, alternatively, recombinant peptides may be generated as fusion proteins to increase antigenicity. As will be further appreciated by those skilled in the art, such antigenic peptides may be screened based upon their ability to induce anti PTH antibody. In this respect, such screening techniques may include, but not limited to, immunoprecipitation or immunoassay.

Once derived, such peptide antigens may then be utilized to generate the antibodies of the present invention using conventional techniques. In this regard, the peptide antigen (s), preferably in combination with an adjuvant, is/are administered to a host animal 24, which preferably comprises a goat. It should be recognized, however, that other species, such as rabbits, mice, sheep, chicken, etc., may additionally be utilized as host animals. In this respect, the administration of such antigens may be accomplished by any of a variety of methods, including but not limited to subcutaneous or intramuscular injection. As will be appreciated, the dose of peptide antigen administered will correspondingly vary with the specific peptide utilized, as well as the animal host. As will additionally be recognized, however, in order to obtain antibodies possessing the highest affinity and specificity possible for a given species, separate antibodies should be generated against the appropriate comparable peptide from each species.

Once administered, the results of antibody titers produced in the host animal are then monitored 26, which may be conducted by any of a variety of techniques well-known in the art, such as routine bleeds and the like, with the antisera being isolated (e.g., via centrifugation), in step 28, and thereafter screened for the presence of anti-peptide antibodies having a binding affinity therefor. It will further be recognized that given the foregoing conventional immunological methods for deriving the antibodies of the present invention, such antibodies may be monoclonal or polyclonal in nature. Consistent with conventional practice it is preferred that the antisera be derived from a plurality of host animals.

The resultant antisera derived from the host animal may be affinity purified to derive the antibodies for the present invention. As is well-known in the art, the antisera may be purified via conventional techniques, such as the introduction into a separation column with the aforementioned antigenic peptides corresponding to amino acid residue sequences 2–12, 1–12, 2–15 and/or 1–15 of PTH being bound to a solid phase (e.g., beads and the like). The antiserum may then be washed to remove antibodies not having specificity for the antigenic peptide or peptides, with the remaining bound antibody, specific for the antigenic peptide or peptides, ultimately being eluted therefrom. Such antibody may then be stored per conventional practices well-known to those skilled in the art.

Advantageously, because the antibodies that are ultimately isolated will have specificity for that antigenic region of PTH corresponding to amino acid residue sequences 2–12, 1–12, 2–15 and 1–15, or any combination thereof, the yield of antibodies generated via the methods of the present invention is believed to be substantially higher than antibodies produced via prior art methods whereby antibodies specific to smaller N-terminal sequences are generated. In this regard, due to the fact that the antibodies ultimately derived will be specific for amino acid residues extending beyond the first six (6) to eight (8) amino acid residues at the N-terminal of PTH provides a greater antigenic tertiary structure for which such antibodies have developed an affinity, whether it would be the entire 1–15 amino acid sequence or any portion thereof.

Moreover, to the extent such antibodies are isolated using those antigenic peptides corresponding to amino acid residue sequences 2–12 and 2–15 of PTH, respectively, there will thus correspondingly be isolated antibodies that have not necessarily acquired a binding affinity, much less a maximum binding affinity, for the first amino acid residue of PTH, which is known to be problematic of antibodies derived via prior art methods. Along these lines, the elimination or substantial suppression of antibodies having an affinity for the first amino acid residue of PTH will likewise be achieved by utilizing peptide sequences corresponding to 1–12 and 1–15, respectively, of PTH provided that such sequences are selected from those species having a dissimilar first amino acid residue from the species for which the antibodies ultimately derive will be utilized. For example, in order to derive antibodies suitable for detecting PTH levels in humans that lack in affinity for the first amino acid residue of human PTH, it will be recognized that the antisera derived from the host animal may be purified against peptides corresponding to amino acid residue sequences 1–12 and 1–15 of rat PTH. As will be understood, because the first N-terminal amino acid residue of rat PTH comprises ALA, as opposed to SER found in humans, any antibodies ultimately isolated will necessarily possess a binding affinity for the amino acid residues extending beyond such first amino acid residue sequence.

Once derivatized in step 30, such antibodies may be used in immunological techniques to correlate the presence of bioactive intact PTH as may be found in a given sample (e.g., serum or plasma). In this respect, the antibodies of the present invention may be used alone or in combination to screen a given sample to determine the presence of bioactive intact PTH but yet advantageously avoid cross-reactivity with the large non (1–84) PTH fragments. By way of example, such antibodies may be incorporated into an immunological assay kit. Exemplary of such applications include the human bioactive intact PTH and rat bioactive intact PTH ELISA kits, produced by Immutopics, Inc., of San Clemente, Calif. which provide an enzyme-linked immunosorbent assay (ELISA) for the quantitative determination of bioactive intact PTH levels in serum, plasma or cell culture media. In this regard, given the foregoing applicability to derive antibodies specific to PTH for a variety of species, it will be recognized that such immunological assay kits, such as those provided by Immutopics, Inc., may be specifically designed such that the affinity and specificity of such antibodies apply to a wide variety of species or alternatively, generated against the appropriate comparable peptide of a given species such that the kits are specific for such species.

Additional modifications and improvements of the present invention may also be apparent to those of ordinary skill in the art. Thus, the particular combination of parts described and illustrated herein is intended to represent only a certain embodiment of the present invention, and is not intended to serve as a limitation of alternative devices within the spirit and scope of the invention.

What is claimed is:

1. A method for producing an antibody to the N-terminal portion of (1–84) PTH useful in the determination of intact PTH 1–84 levels in a biological sample, the method comprising the steps:

a) administering a first peptide antigen alone or a first peptide antigen coupled to a carrier protein to a host animal to induce antibody production against said first peptide antigen in said host animal, said first peptide antigen being selected from the group consisting of SEQ ID NO. 3, SEQ ID NO. 4, SEQ ID NO. 5, SEQ ID NO. 6, (1–34) PTH and (1–84) PTH;

b) monitoring antibody titer produced by said administration of said peptide antigen to said host animal;

c) extracting antisera produced in said host animal; and d) isolating and selecting at least one antibody from said antisera extracted in step c) by affinity chromatography utilizing a second peptide antigen selected from the group consisting of SEQ ID NO. 3, SEQ ID NO. 4, SEQ ID NO. 5, and SEQ ID NO. 6.

2. The method of claim 1 wherein in step a), said host animal is selected from the group consisting of a mouse and a rabbit.

3. The method of claim 1 wherein in step a), said host animal comprises at least one goat.

4. The method of claim 1 wherein in step a), said (1–84) PTH is derived from a species selected from the group consisting of a human, a rat, a mouse, a bovine, a dog, and a pig.

5. The method of claim 1 wherein step a), said (1–84) PTH is from a species selected from the group consisting of a human, a rat, a mouse, a bovine, a dog and a pig.

* * * * *

UNITED STATES PATENT AND TRADEMARK OFFICE
CERTIFICATE OF CORRECTION

PATENT NO. : 6,838,264 B2
DATED : January 4, 2005
INVENTOR(S) : Richard J. Zahradnik and Jeffrey R. Lavigne It is certified that error appears in the above-identified patent and that said Letters Patent is hereby corrected as shown below:

Drawings
Figure 1, position 56, for RAT sequence delete "ASP" and insert UNDERLINED type style -- GLU --.
Figure 2, position 56, for RAT sequence delete "ASP" and insert -- GLU --.
Figure 2, position 56, for MOUSE sequence DELETE THE UNDERLINE ONLY of "GLU".
Figure 2, position 56, for BOVINE sequence ADD THE UNDERLINE to -- ASP --.
Figure 2, position 56 for HUMAN sequence ADD THE UNDERLINE to -- ASP --.
Figure 2, position 56 for CANINE sequence ADD THE UNDERLINE to -- ASP --.
Figure 2, position 56 for PORCINE sequence ADD THE UNDERLINE to -- ASP --.

Column 3,
Line 5, delete "1 FU" and insert -- LEU --.

Column 5,
Line 52, delete "2-12" and insert -- 2-12 --.

Column 6,
Line 11, delete "A1A" and insert -- ALA --.
Line 12, delete "will he readily" and insert -- will be readily --.

Column 14,
Line 36, delete "(1-84)" and insert -- (1-34) --.

Signed and Sealed this

Twenty-eighth Day of February, 2006

JON W. DUDAS
*Director of the United States Patent and Trademark Office*

SEQUENCE LISTING

```
<160> NUMBER OF SEQ ID NOS: 12

<210> SEQ ID NO 1
<211> LENGTH: 11
<212> TYPE: PRT
<213> ORGANISM: Artificial Sequence
<220> FEATURE:
<223> OTHER INFORMATION: Induces Formation of Antibodies and Isolates
      said Antibodies

<400> SEQUENCE: 1

Val Ser Glu Ile Gln Leu Met His Asn Leu Gly
 1               5                  10

<210> SEQ ID NO 2
<211> LENGTH: 11
<212> TYPE: PRT
<213> ORGANISM: Artificial Sequence
<220> FEATURE:
<223> OTHER INFORMATION: Induces Formation of Antibodies and Isolates
      said Antibodies

<400> SEQUENCE: 2

Val Ser Glu Ile Gln Phe Met His Asn Leu Gly
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Induces Formation of Antibodies and Isolates
      said Antibodies

<400> SEQUENCE: 3

Ser Val Ser Glu Ile Gln Leu Met His Asn Leu Gly
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Induces Formation of Antibodies and Isolates
      said Antibodies

<400> SEQUENCE: 4

Ser Val Ser Glu Ile Gln Phe Met His Asn Leu Gly
 1               5                  10

<210> SEQ ID NO 5
<211> LENGTH: 12
<212> TYPE: PRT
<213> ORGANISM: Artificial Sequence
```

-continued

```
<220> FEATURE:
<223> OTHER INFORMATION: Induces Formation of Antibodies and Isolates
      said Antibodies

<400> SEQUENCE: 5

Ala Val Ser Glu Ile Gln Leu Met His Asn Leu Gly
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Induces Formation of Antibodies and Isolates
      said Antibodies

<400> SEQUENCE: 6

Ala Val Ser Glu Ile Gln Phe Met His Asn Leu Gly
 1               5                  10

<210> SEQ ID NO 7
<211> LENGTH: 14
<212> TYPE: PRT
<213> ORGANISM: Artificial Sequence
<220> FEATURE:
<223> OTHER INFORMATION: Induces Formation of Antibodies and Isolates
      said Antibodies

<400> SEQUENCE: 7

Val Ser Glu Ile Gln Leu Met His Asn Leu Gly Lys His Leu
 1               5                  10

<210> SEQ ID NO 8
<211> LENGTH: 14
<212> TYPE: PRT
<213> ORGANISM: Artificial Sequence
<220> FEATURE:
<223> OTHER INFORMATION: Induces Formation of Antibodies and Isolates
      said Antibodies

<400> SEQUENCE: 8

Val Ser Glu Ile Gln Phe Met His Asn Leu Gly Lys His Leu
 1               5                  10

<210> SEQ ID NO 9
<211> LENGTH: 15
<212> TYPE: PRT
<213> ORGANISM: Artificial Sequence
<220> FEATURE:
<223> OTHER INFORMATION: Induces Formation of Antibodies and Isolates
      said Antibodies

<400> SEQUENCE: 9

Ser Val Ser Glu Ile Gln Leu Met His Asn Leu Gly Lys His Leu
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: Induces Formation of Antibodies and Isolates
      said Antibodies

<400> SEQUENCE: 10

Ser Val Ser Glu Ile Gln Phe Met His Asn Leu Gly Lys His Leu
 1               5                  10                  15
```

-continued

```
<210> SEQ ID NO 11
<211> LENGTH: 15
<212> TYPE: PRT
<213> ORGANISM: Artificial Sequence
<220> FEATURE:
<223> OTHER INFORMATION: Induces Formation of Antibodies and Isolates
      said Antibodies

<400> SEQUENCE: 11

Ala Val Ser Glu Ile Gln Leu Met His Asn Leu Gly Lys His Leu
 1               5                  10                  15

<210> SEQ ID NO 12
<211> LENGTH: 15
<212> TYPE: PRT
<213> ORGANISM: Artificial Sequence
<220> FEATURE:
<223> OTHER INFORMATION: Induces Formation of Antibodies and
      Isolates said Antibodies

<400> SEQUENCE: 12

Ala Val Ser Glu Ile Gln Phe Met His Asn Leu Gly Lys His Leu
 1               5                  10                  15
```